US007049084B2

(12) United States Patent
Zhang et al.

(10) Patent No.: US 7,049,084 B2
(45) Date of Patent: May 23, 2006

(54) NEUROBLASTOMA CELL LINES EXPRESSING THE α2δ SUBUNIT OF CALCIUM CHANNELS AND METHODS THEREFORE

(75) Inventors: Sui-Po Zhang, Bala Cynwyd, PA (US); Susan K. Yagel, Hatfield, PA (US); Ellen E. Codd, Blue Bell, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 216 days.

(21) Appl. No.: 09/870,338

(22) Filed: May 30, 2001

(65) Prior Publication Data

US 2002/0192728 A1 Dec. 19, 2002

(51) Int. Cl.
*G01N 33/574* (2006.01)
*G01N 33/53* (2006.01)

(52) U.S. Cl. ........................... 435/7.23; 435/7.1
(58) Field of Classification Search .................. 435/6, 435/7.1
See application file for complete search history.

(56) References Cited

U.S. PATENT DOCUMENTS

| 5,401,629 A | 3/1995 | Harpold et al. |
| 6,013,474 A | 1/2000 | Ellis et al. |
| 6,090,631 A | 7/2000 | Catterall et al. |
| 2003/0073132 A1* | 4/2003 | Bertelli et al. |

FOREIGN PATENT DOCUMENTS

WO   WO 00/20450   *   4/2000

OTHER PUBLICATIONS

Gotti et al. Cholinergic receptors, ion channels, neurotransmitter synthesis, and neurite outgrowth are independently regulated during the in vitro differentiation of a human neuroblastoma cell line Differentiation vol. 34 1987.*

Alden, K.J., et al, "Differential Effect of Gabapentin on Neuronal and Muscle Calcium Currents", Journal of Pharmacology and Experimental Therapeutics, 2001 vol. 297:727:-735.

Angeloni, D., et al, A G-to-A single nucleotide polymorphism in the human Alpha 2 Delta 2 calcium channel subunit gene that maps at chromosome 3p21.3, Molecular and Cellular Probes 2000 vol. 14:53-54.

Backonja, M., et al. "Gabapentin for the Symptomatic Treatment of Painful Neuropathy in Patients With Diabetes Mellitus," JAMA 1998 vol. 280:1831-1836.

Brown, J.P., et al. "Cloning and Deletion Mutagenesis of the α2δ Calcium Channel Subunit from Porcine Cerebral Cortex", Journal of Biological Chemistry 1998 vol. 273:25458-25465.

Bruhn, T.O., et al. "Activation of Thyrotropin-Releasing Hormone Gene Expression in Cultured Fetal Diencephalic Neurons by Differentiating Agents", 1996 Endocrinology vol. 137:572-579.

Carbone, E.., et al. "Ca currents in human neuroblastoma IMR32 cells: kinetics, permeability and pharmacology", Pflugers Arch 1990 vol. 416:170-179.

Clementi, F., et al. "Cell Plasticity During in vitro Differentiation of a Human Neuroblastoma Cell Line", Adv.Exp. Med. Biol. 1991 vol. 296:91-102.

Dissanayake, V.U.K., et al. "Spermine modulation of specific {3H}-gabapentin binding to the detergent-solubilized porcine cerebral cortex α2δ calcium channel subunit" British Journal of Pharmacol. 1997 vol. 120:833-840.

Dooley, D.J., et al. "Inhibition of K+ -evoked glutamate release from rat neocortical and hippocampal slices by gabapentin", Neuroscience Letters 2000 vol. 280:107-110.

Fink, K., et al. "Inhibition of neuronal Ca2+ influx by gabapentin and subsequent reduction of neurotransmitter release from rat neocortical slices", British Journal of Pharmacology 2000 vol. 130:900-906.

Gao, B. et al. Functional Properties of a New Voltage-dependent Calcium Channel α2δ Auxiliary Subunit Gene (CACNA2D2) Journal of Biological Chemistry 2000 vol. 275:12237-12242.

Gee, N.S., et al. "The Novel Anticonvulsant Drug, Gabapentin (Neurontin) Binds to the α2δSubunit of a Calcium Channel", The Journal of Biological Chemistry 1996 vol. 271:5768-5776.

(Continued)

*Primary Examiner*—Nancy Vogel
(74) *Attorney, Agent, or Firm*—Laura Donnelly

(57) ABSTRACT

The present invention provides methods for identifying test substances that bind to the α2δ subunit of a calcium channel.

8 Claims, 5 Drawing Sheets

OTHER PUBLICATIONS

Gotti, C., et al. "Cholinergic receptors, ion channels, neurotransmitter synthesis, and neurite outgrowth are independently regulated during the in vitro differentiation of a human neuroblastoma cell line," Differentiation 1987 vol. 34:144-155.

Hill, D.R., et al. "Localization of {3H} gabapentin to a novel site in rat brain: autoradiographic studies", European Journal of Pharmacology, 1993 Molecular Pharmacology Section vol. 244:303-309.

Hogg, J.E., et al "The human neuroblastoma cell line, IMR-32, expresses functional corticotropin-releasing factor recptors", European Journal of Pharmacology 1996 vol. 312:257-261.

Kurata, S. et al., "Human neuroblastoma cells produce the NF-κB like HIV-1 transcription activator during differentiation," Federation of European Biochemical Societies 1993 vol. 321:201-204.

Laird, M. A., et al. "Use of Gabapentin in the Treatment of Neuropathic Pain", The Annals of Pharmacotherapy 2000 vol. 34:802-807.

Marais, E., et al. "Calcium Channel α2δ Subunites—Structure and Gabapentin Binding", Molecular Pharmacology 2001 vol. 59:1243-1248.

McEnery, M.W., et al. "β1B subunit of voltage-dependent Ca2+channels is predominant isoform expressed in human neuroblastoma cell line IMR32", FEBS letters 1997 vol. 420:74-78.

Rowbotham, M., et al. "Gabapentin for the Treatment of Postherpetic Neuralgia", JAMA 1998 vol. 280:1837-1842.

Shistik, E., et al. "Ca2+ current enhancement by α2/δ and β subunits in Xenopus oocytes: contribution of changes in channel gating and α1 protein level", Journal of Physiology 1995 vol. 489:55-62.

Stefani, A., et al., "Gabapentin inhibits calcium currents in isolated rat brain neurons", Neurophamacology 1998 vol. 37:83-91.

Thurlow, R.J., et al. "{3H} Gabapentin may label a system-L-like neutral amino acid carrier in brain", European Journal of Pharmacology, 1993 vol. 247. 341-345.

Thurlow, R.J., et al. "Comparison of the autoradiographic binding distribution of {3H}-gabapentin with excitatory amino acid receptor and amino acid uptake site distributions in rat brain", British Journal of Pharmacology 1996 vol. 118:457-465.

Walker, D. et al., "Subunit interaction sites in voltage-dependent Ca2+" channels: role in channel function, Trends Neurosceicne 1998 vol. 21:148-154.

Wang, M., et al, "Structural requirement of the calcium-channel subunit α2δ for gabapentin binding", Biochem J. 1999 vol. 342:313-320.

PCT International Search Report, PCT/US02/16732 Mar. 14, 2003.

European Search Report dated Jul. 22, 2004, for corresponding EP application 02737215.0.

Tarroni et al, "Anti-beta-2 subunit antisense oligonucleotides modulate the surface expression of the alph-1 subunit of N-type omega-CTX sesitive Ca-2+ channels in IMR 32 human neuroblastoma cells", Biochemical and Biophysical Research Communications, vol. 201, No. 1 (1994) pp. 180-185.

Wyatt et al, "The effect overexpression of auxillary Ca2+ channel subunits on native Ca2_ channel currents in undifferentiated mammalian NG108-15 cells", Journal of Physiology, vol. 510, No. 2 (Jul. 15, 1998) pp. 347-360.

Brown et al, "Isolation of the (3H)gabapentin-binding protein/alpha2delta Ca2+ channel subunit from porcine brain: Development of a radioligand binding assay for alpha2delta subunits using (3H) leucine", Analytical Biochemistry, vol. 255, No. 2 (Jan. 15, 1998) pp. 236-243.

* cited by examiner

FIGURE 2 – PANEL A
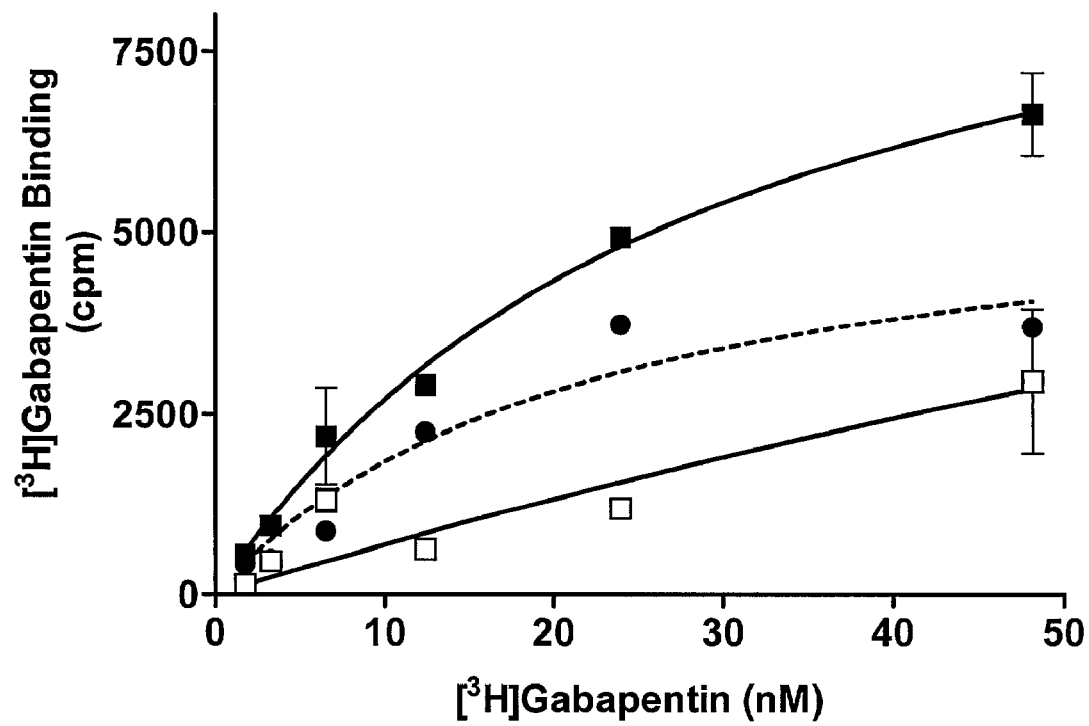

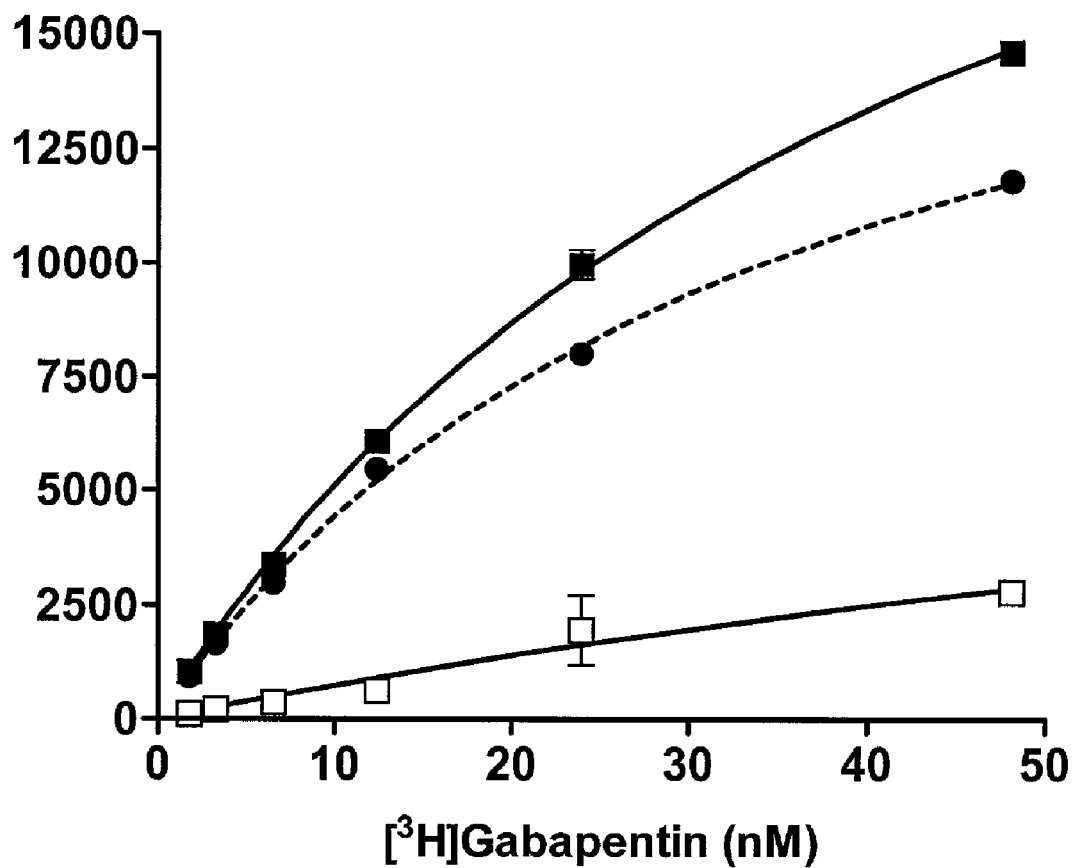
FIGURE 2 – PANEL B

FIGURE 2 – PANEL C
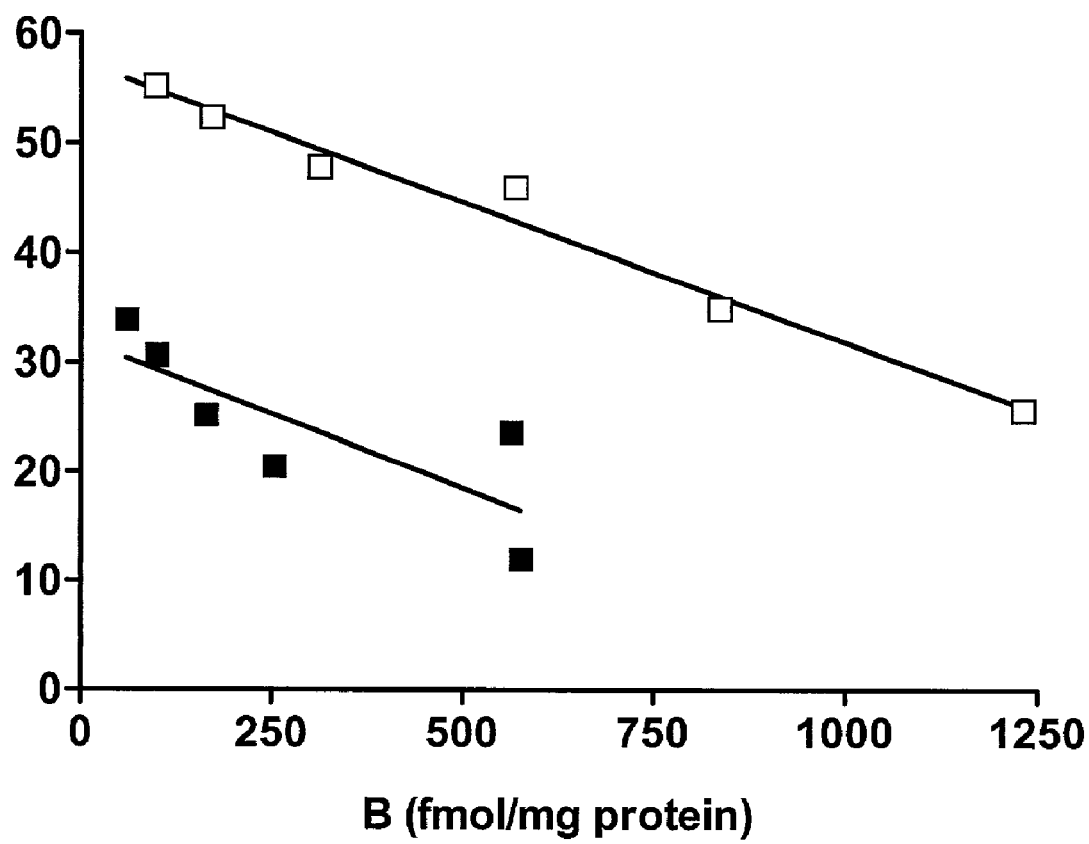

NEUROBLASTOMA CELL LINES EXPRESSING THE α2δ SUBUNIT OF CALCIUM CHANNELS AND METHODS THEREFORE

FIELD OF THE INVENTION

The present invention relates to neuroblastoma cells that express the α2δ subunit of the calcium channel. In another aspect of this invention, the invention relates to methods and assays using neuroblastoma cells and neuroblastoma cell membranes. The cells of the present invention are useful for discovering new compounds that modulate the function of the α2δ subunit of calcium channel.

BACKGROUND OF THE INVENTION

Several subtypes of the α2δ subunit of calcium channel have been cloned (Angeloni et al. *Mol. Cell. Probes* 14:53–54, 2000; Gao et al., *J. Biol. Chem.* 275:12237–12242, 2000; and PCT Application WO 99/23519).

Neuroblastoma cell membranes contain N-type calcium channels and neuroblastoma cells have been used as a model for neuronal differentiation (Bruhn, et al. *Endocrinology* 137:572–9, 1996; Gotti, et al. *Differentiation (Berlin)* 34:144–55, 1987; Hogg et al. *Pharmacol.,* 312:257–261, 1996; and Kurata, et al. *FEBS Lett.,* 321:201–4, 1993). 5-Bromo-2'-deoxyuridine (BrdU) induces morphological and functional differentiation of neuroblastoma cells, resulting in an increase of neurotransmitter receptors and the release of neurotransmitters (Clementi, et al. *Adv. Exp. Med. Biol.* 296:91–102, 1991). [$^{125}$I]ω-conotoxin binding sites were increased in the differentiated neuroblastoma IMR32 cells, indicating that the N-type calcium channels were increased in the cells (Carbone et al., *Pfluegers Arch.,* 416:170–9, 1990). Recently, Western blot analysis has shown that the β1b subunit of calcium channels is the predominant isoform expressed in IMR32 cells (McEnery, et al. *FEBS Lett.* 420: 74–78, 1997).

Gabapentin (GBP) is an anticonvulsant that has shown usefulness in the treatment of neuropathic pain (Backonjy, M. et al. *J. Am. Med. Assoc.* 280:1831–1836, 1998; Laird and Gidal, *Ann. Pharmacother.* 34:802–807, 2000; and Rowbotham et al. M., *J. Am. Med. Assoc.,* 280:1837–1842, 1998). GBP inhibits neurotransmitter release (Dooley, et al. *Neurosci. Lett.* 280:107–110, 2000) and inhibits calcium currents in brain neurons (Fink, et al. *Br. J. Pharmacol.* 130:900–906, 2000; Larid and Gidal, supra; and Stefani et al. *Neuropharmacology* 37:83–91, 1998). Interestingly, a high-affinity binding site for GBP was found in brain tissue and the target protein was identified as the α2δ subunit of subunit of calcium channels (Brown and Gee, *J. Biol. Chem.,* 273:25458–25465, 1998; Dissanayake, et al. *Br. J. Pharmacol.,* 120:833–840, 1997; and Gee et al., *J. Biol. Chem.* 271:5768–76, 1996). An autoradiographic binding study showed that the GBP binding site was widely distributed in rat brain areas such as frontal cortex, striatum, hippocampus and cerebellum (Hill and Woodruff, *Eur. J. Pharmacol. Mol. Pharmacol. Sect.,* 244:303–9, 1993; Thurlow et al. *Br. J. Pharmacol.,* 118;457–465, 1996). Therefore compounds that compete with Gabapentin binding to the α2δ subunit should be useful as anticonvulsants and in the treatment of neuropathic and chronic pain.

SUMMARY OF THE INVENTION

The present invention relates to a method for detecting binding of a test substance to an α2δ subunit comprising the steps of: contacting a neuroblastoma cell membrane sample comprising the α2δ subunit with gabapentin and a test substance; detecting binding of gabapentin to the cell membrane; and, comparing the level of binding of gabapentin as compared with a control sample lacking the test substance.

In one embodiment the cell membranes are part of intact cells and in another embodiment the cell membranes are obtained from isolated cell membrane preparations. In one embodiment the cells are the neuroblastoma cells IMR32. Preferably the neuroblastoma cell membranes are differentiated neuroblastoma cell membranes and in one embodiment the differentiated cell membranes are obtained following cell incubation with BrdU.

In a preferred method, the methods of this invention further comprise the step of separating the cell membranes from unbound gabapentin. In another preferred method, the comparing step comprises measuring binding of labeled gabapentin bound to the cell membranes. The invention further relates to compounds identified using the methods of this invention.

In another embodiment the invention further relates to a test substance identified by a method comprising the steps of: contacting a neuroblastoma cell membrane sample comprising the α2δ subunit of a calcium channel with gabapentin and a test substance; detecting binding of the gabapentin to the cell membrane; and comparing the level of binding of gabapentin as compared with a control sample lacking the test substance.

The invention further relates to a method for identifying a test substance capable of binding to an α2δ subunit of a calcium channel comprising the steps of: incubating an IMR32 cell membrane with radioactive gabapentin (GBP) and a test substance, wherein the membrane comprises an α2δ subunit of calcium channel and where the contact is for sufficient time to allow GBP binding to the α2δ subunit of calcium channels in the cell membranes; separating the cell membranes from unbound radioactive GBP; measuring binding of the radioactive GBP to the cell membranes; and identifying a compound that inhibits GBP binding by a reduction of the amount of radioactive GBP in the measuring step to an established control.

The methods of the present invention are useful for identifying compounds that interact with the α2δ subunit of calcium channels. Compounds identified using the methods of the present invention can then be tested for their ability to treat biological conditions mediated by the α2δ subunit of calcium channels.

BRIEF DESCRIPTION OF THE DRAWINGS

FIG. 2. Saturation binding of [$^3$H]GBP to IRM32 cell membranes. (A) Varying concentrations of [$^3$H]GBP were incubated with membranes (40 μg protein/ml) from non-differentiated IMR32 cells. Black squares=Total bound counts; Black circles=Specific binding; Clear squares=nonspecific binding.

Figure 1:
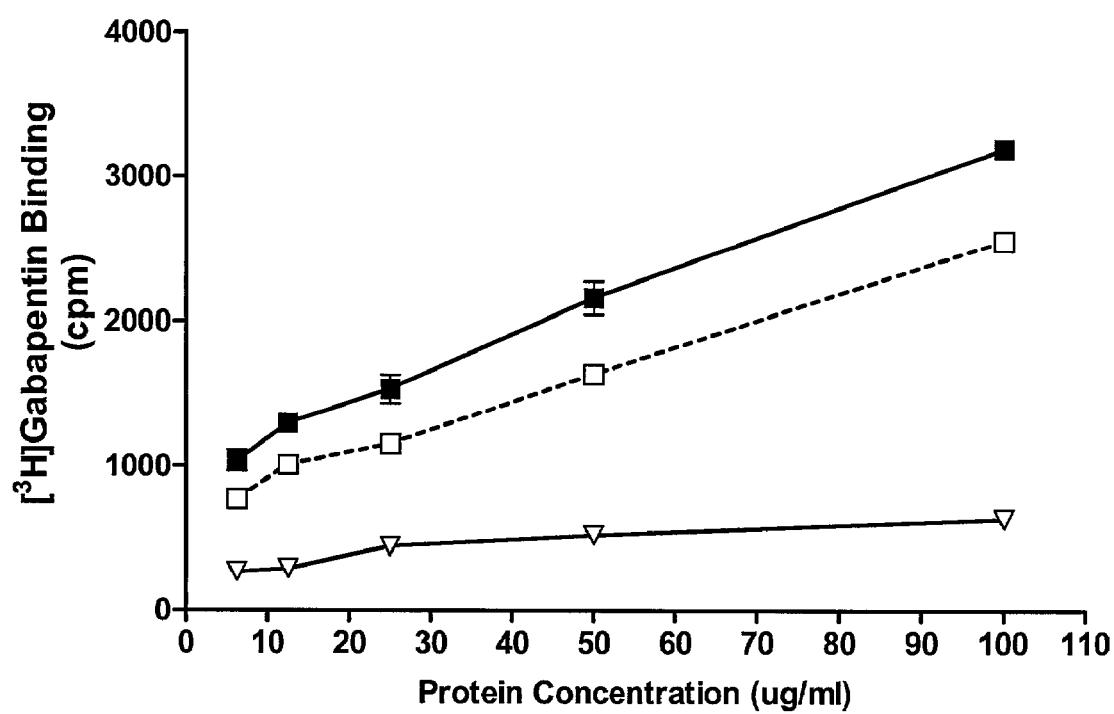
FIG. 1. Effect of membrane protein concentration on [$^3$H]GBP binding. The membranes of human neuroblastoma IMR32 cells were incubated with [$^3$H]GBP (10 nM) at 25° C. for 60 min. The data are representative of two experiments with each point assayed in duplicate. Black squares=Total bound counts; Clear squares=Specific binding; Clear triangles=nonspecific binding.

(B) Varying concentrations of [$^3$H]GBP were incubated with membranes (40 µg protein/ml) from IMR32 cells differentiated by 10 µM BrdU. Black squares=Total bound counts; Black circles=Specific binding; Clear squares=nonspecific binding.

(C) Scatchard plot from the data of FIG. 2A and FIG. 2B. Clear squares=differentiated IMR32 cells; Black squares=nondifferentiated IMR32 cells FIG. 3. Inhibition of [$^3$H]GBP binding to human neuroblastoma IMR32 cell membranes by GBP and L-methionine. Varying concentrations of unlabeled GBP and L-methionine were incubated with membranes (20 µg protein/ml) of non-differentiated and differentiated IMR32 cells in the presence of 10 nM [$^3$H]GBP. The results shown represent two experiments with each point assayed in duplicate. Black squares=GBP binding to nondifferentiated IMR32 cells; Black triangles=L-methionine binding to nondifferentiated IMR32 cells; Clear squares=GBP binding to differentiated IMR32 cells; Clear triangles=L-methionine binding to differentiated IMR32 cells

DETAILED DESCRIPTION OF THE INVENTION

The present invention provides methods to identify compounds that modulate the function of the α2δ subunit of the calcium channel in neuroblastoma cells and preferably in differentiated neuroblastoma cells.

There are a variety of neuroblastoma primary cells and cell lines that can be used in the methods of this invention. For purposes of this invention the term "neuroblastoma cell lines" includes cell lines, cells isolated from tumor explants and cell hybrids prepared by fusion of a cell with a neuroblastoma cells. Preferred neuroblastoma cells of the present invention are of human origin but can also be of animal origin. Exemplary cells and cells lines include, but are not limited to, IMR32 cells, SK-N-MC cells and NG 108 cells (a mouse neuroblastoma/rat glioma hybrid cell line). These cells are available from a number of sources including the ATCC (Manassas, Va.). While established cell lines are preferred, cells useful for this invention can also be isolated from a variety of vertebrate sources, such as animal or human tumor explants.

In a preferred embodiment, IMR32 cells are used and in another preferred embodiment the neuroblastoma cells are exposed to a differentiation-promoting agent, such as BrdU. Other differention-promoting agents that can be used in this invention include, but are not limited to, dibutryl cyclic AMP, neural growth factor (NGF) and retinoic acid. Differentiated neuroblastoma cells tend to express increased levels of α2δ subunit protein as compared with undifferentiated cells.

There are a number of methods known in the literature for differentiating undifferentiated neuronal cells, such as neuroblastoma cells, and an exemplary method is found in the example section, provided below. In general, however, the cells are exposed to a non-cytotoxic amount of the differentiation-promoting agent for a time sufficient to induce differentiation in the cell culture. Differentiation can be determined visually, through the outgrowth of neural processes, for example, or in the expression of a more differentiated phenotype, including increased adherence to the substrate, improved growth control and a general flattening of the cell morphology. Alternatively, cell differentiation can be determined by detecting proteins that are known to be associated with a more differentiated cell phenotype, as is known in the art.

The assays of this invention can be used as intact cell assays or the assays can be performed using membrane lysates or purified membrane preparations from cells expressing the calcium channel α2δ subunit. Where cells membranes are used, the α2δ subunit of calcium channels is isolated as a component of the neuroblastoma cell membranes. Isolated cell membranes are prepared using conventional means such as homogenizing the cells via mechanical force.

Gabapentin (GBP) (CAS number 60142-96-3) is used as a specific ligand for the α2δ subunit of calcium channels. In a preferred embodiment the GBP is labeled to facilitate detecting GBP binding to the α2δ subunit. GBP can be labeled using any number of methods known in the art including fluorescent labels, radioactive labels, and the like. In a preferred embodiment, a commercially available [$^3$H] GBP is used as a detectable ligand in the displacement assays of the present invention.

In the assays of the present invention, the cell membranes are combined with GBP and a test substance. The test substance can be any candidate molecule that one hypothesizes will bind to the α2δ subunit. These include small molecules, peptides, polypeptides, including antibodies, and the like.

The cell membrane mixture comprising GBP and the test substance are then incubated in an aqueous buffer for a time sufficient to permit the GBP to bind to the α2δ subunit contained in the cell membranes. The amount of incubation time necessary depends on the amount of reagents used, temperature, and other factors. Varying the reaction conditions using methods well known in the art alters the amount of label incorporation into the cell membranes and these conditions can be readily optimized by those of ordinary skill in the art. After incubation the cell membranes are isolated from unbound GBP using conventional means, including filtration or centrifugation.

The ability of the test substance to bind to the α2δ subunit is determined by measuring a reduction in the amount of GBP binding to the cell membranes in samples containing both GBP and test substance as compared to a control reaction that does not include the test substance and which preferably includes both unlabeled and labeled GBP. Where the GBP is radiolabeled, the level of radioactivity in treated cell membranes compared to control membranes is measured.

Candidate compounds that are capable of competing with GBP for binding are identified using the methods of the present invention. These compounds can then be tested for their ability to affect a number of biological conditions mediated by the α2δ subunit of calcium channels.

The present invention is exemplified by way of the following examples. These examples are not intended to limit the present invention.

EXAMPLE 1

Differentiation of IMR32 Cells and Analysis of the Expression of the α2δ Subunit of Calcium Channels Materials and Methods IMR32 cells, SK-N-MC cells and NG 108 cells as well as cells treated in culture with 10 µM of BrdU for 10 to 12 days were used. Cells were harvested and homogenates were made in HEPES/KOH buffer, pH 7.4. The homogenates were centrifuged for 15 min at 1000×g, and the supernatants were centrifuged at 40000×g for 15 min to obtain cell membranes.

A [$^3$H]GBP binding assay was performed as described by Gee, et al. (supra). Non-specific binding was defined in the presence of 100 μM unlabeled GBP. Separation of bound from free ligand was effected by filtration through 0.3% polyethylenimine-soaked GF/B filters. The filters were washed with 3×4 ml of 10 mM HEPES pH 7.4. Radioactivity on filters was determined by scintillation counter.

[$^3$H]GBP binding increased with increasing concentrations of cell membranes. [$^3$H]GBP bound to cell membranes from all neuroblastoma cell lines tested. The increase in binding was linear with membrane concentrations up to 100 μg protein/ml (FIG. 1).

In one example to test the effect of BrdU on the density of [$^3$H]GBP binding sites in the differentiated IMR32 cells, saturation experiments were performed using both undifferentiated and differentiated IMR32 cell membranes (FIG. 2). Scatchard analysis of the saturation binding data suggests a single high affinity GBP binding site on IMR 32 cell membranes with a $K_d$ value of 37 nM and $B_{max}$ value of 1186 fmol/mg protein. BrdU increased the expression of [$^3$H]GBP binding sites ($B_{max}$=2245 fmol/mg protein) without changing its affinity ($K_d$=39 nM).

Figure 3:
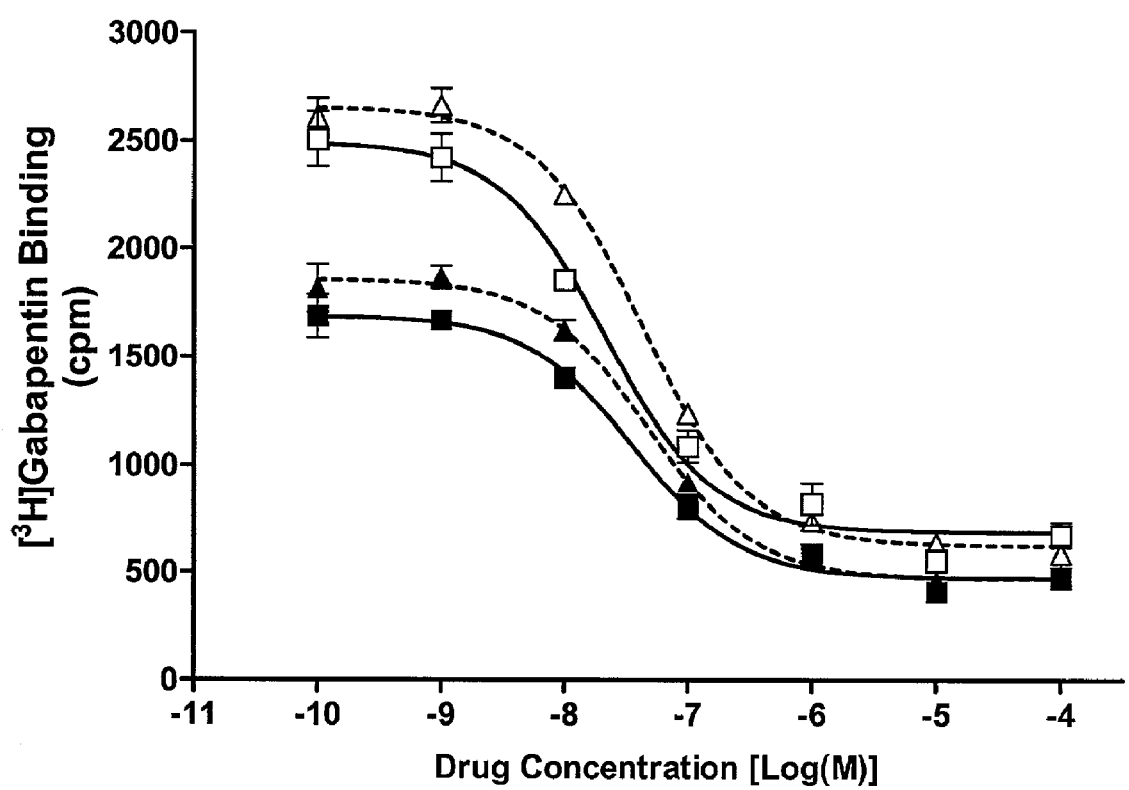

The pharmacology of [$^3$H]GBP binding sites was examined by investigating the ability of unlabeled GBP and L-methionine to inhibit binding. 10 nM of [$^3$H]GBP was used for the experiments. The $K_i$ values were obtained using a one-site binding model and are summarized in Table 1. FIG. 3 shows that unlabeled GBP and L-methionine dose-dependently inhibited [$^3$H]GBP binding to IMR32 cell membranes. BrdU did not significantly alter the $K_i$ values of GBP and L-methionine for the cell membranes (Table 1).

TABLE 1

$K_i$ values of GBP and L-methionine inhibition of [$^3$H]GBP binding to undifferentiated (Control) and differentiated (BrdU) IMR32 cell membranes.

| | $K_i$ (nM) | |
|---|---|---|
| | Control | BrdU |
| GBP | 29 | 15 |
| L-methionine | 39 | 30 |

The increase in [$^3$1H]GBP binding by BrdU in neuroblastoma cells suggests that the α2δ subunit of calcium channels increases during the differentiation of human neuroblastoma cells. This increase, in addition to previous results, which indicated that the α1 and β1b subunits were also increased by BrdU (Carbone, et al., supra and McEnery et al., supra), suggests that most of the major subunits of calcium channels are up-regulated during the differentiation of human neuroblastoma cells. Full activation of calcium channels requires both β and α2δ subunits (Shistik, et al. *J. Physiol.* (London): 489:55–62, 1995 and Walker and DeWaard, *Trends Neurosci.*, 21:148–154, 1998). The present results imply that calcium channels play an important role in the differentiation of human neuroblastoma cells.

Several L-amino acids, such as leucine, methionine, phenylalanine and valine, inhibit [$_3$H]GBP binding to synaptic plasma membranes. L-methionine is one of the most potent inhibitors (Thurlow, et al., *Eur. J. Pharmacol. Mol. Pharmacol. Sect.*, 247:341–5, 1993). We found that GBP and L-methionine inhibited [$^3$H]GBP binding to IMR32 cell membranes. The $K_i$ values of GBP and L-methionine were not significantly different between undifferentiated and differentiated cell membranes, indicating that BrdU did not change the affinities of GBP and L-methionine for cell membrane binding.

GBP binding to calcium channels requires both α2 and δ subunits (Wang, et al. *Biochem. J,* 342:313–320, 1999). The region between the N-terminal end and the first transmembrane domain of α2, as well as the region between the splicing acceptor sites may play important roles in maintaining the structural integrity for GBP binding.

What is claimed is:

1. A method for determining the binding of a test substance to an α2δ subunit of a calcium channel comprising the steps of:
    (a) contacting a sample of neuroblastoma cell membranes comprising the α2δ subunit of a calcium channel with gabapentin and a test substance;
    (b) detecting binding of the gabapentin to the cell membranes; and
    (c) comparing the amount of binding of gabapentin of the sample as compared with a control sample lacking the test substance, thereby determining the binding of the test substance to the α2δ subunit.

2. The method of claim 1 wherein the cell membranes are part of intact cells.

3. The method of claim 1 wherein the cell membranes are obtained from an isolated cell membrane preparation.

4. The method of claim 1 wherein the neuroblastoma cell membranes are IMR32, SK-N-MC or NG 108 cell membranes.

5. The method of claim 1 wherein the neuroblastoma cell membranes are differentiated neuroblastoma cell membranes.

6. The method of claim 5 wherein the differentiated cell membranes are obtained following incubation with BrdU.

7. The method of claim 1 further comprising the step of separating the cell membranes from unbound gabapentin.

8. The method of claim 1 wherein the comparing step comprises measuring binding of labeled gabapentin bound to the cell membranes.

* * * * *